United States Patent
Inouye

(10) Patent No.: US 7,241,864 B2
(45) Date of Patent: Jul. 10, 2007

(54) RECOMBINANT PHOTOPROTEINS AND THEIR CONJUGATES

(75) Inventor: Satoshi Inouye, Yokohama (JP)

(73) Assignee: Chisso Corporation, Osaka-shi (JP)

( * ) Notice: Subject to any disclaimer, the term of this patent is extended or adjusted under 35 U.S.C. 154(b) by 543 days.

(21) Appl. No.: 10/400,630

(22) Filed: Mar. 28, 2003

(65) Prior Publication Data

US 2003/0212259 A1   Nov. 13, 2003

(30) Foreign Application Priority Data

Mar. 29, 2002 (JP) ............................. 2002-093849
Jan. 27, 2003 (JP) ............................. 2003-017505

(51) Int. Cl.
G01N 33/53 (2006.01)
C07K 14/435 (2006.01)
C12N 15/12 (2006.01)
C12N 15/63 (2006.01)
C12N 5/10 (2006.01)

(52) U.S. Cl. ...................... 530/350; 435/7.5; 435/69.1; 435/320.1; 435/325

(58) Field of Classification Search ..................... None
See application file for complete search history.

(56) References Cited

OTHER PUBLICATIONS

Lewis and Daunert. Anal Chem. 2001; 73: 3227-3233.*
Paolo F. Zatta, et al. "A Solid-Phase Assay For β-1, 4-Galactosyltransferase Activity in Human Serum Using Recombinant Aequorin" Analytical Biochemistry 194, 1991, pp. 185-191.
J. C. Lewis, et al. Site-Specifically Labeled Photoprotein-Thyroxine Conjugates Using Aequorin Mutants Containing Unique Cysteine Residues: Applications For Binding Assays (Part II) Bioconjugate Chem. 11, 2000, pp. 140-145.
Satoshi Inouye, et al. "Cloning and Sequence Analysis of cDNA for the Luminescent Protein Aequorin" Proc. Natl. Acad. Sci USA, vol. 82, May 1985, pp. 3154-3158.
James F. Head, et al. "The Crystal Structure of the Photoprotein Aequorin at 2.3 Å Resolution" Nature, vol. 405, May 18, 2000, pp. 372-376.
Osamu Shimomura, et al. "Mechanism of the Luminescent Intramolecular Reaction of Aequorin," Biochemistry, vol. 13, No. 16, 1974, pp. 3278-3286.
Kouichi Kurose, et al. "Bioluminescence of the $Ca^{2+}$-Binding Photoprotein Aequorin After Cystein Modification" Proc. Natl. Acad. Sci. USA, vol. 86, Jan. 1989, pp. 80-84.
J. C. Lewis, et al. "Bioluminescence and Secondary Structure Properties of Aequorin Mutants Produced for Site-Specific Cunjugation and Immobilization" Bioconjugate Chem. 11, 2000 pp. 65-70.
Midori Nomura, et al. "A C-Terminal Proline is Required for Bioluminescence of the $Ca^{2+}$-Binding Photoprotein, Aequorin" Federation of European Biochemical Societies, vol. 295, No. 1,2,3, Dec. 1999, pp. 63-66.
Satoshi Inouye, et al. "Overexpression and Purification of the Recombinant $Ca^{2+}$-Binding Protein, Apoaequorin" J. Biochem. 105, 1989, pp. 473-477.
Satoshi Inouye, et al. "High-Level Expression and Purification of Apoaequorin" Protein and Expression and Purification 2, 1991, pp. 122-126.
Osamu Shimomura, et al. "The Relative Rate of Aequorin Regeneration From Apoaequorin and Coelenterazine Analogues" Biochem. J. 296, 1993, pp. 549-551.

* cited by examiner

Primary Examiner—Elizabeth Kemmerer
Assistant Examiner—Christina Borgeest
(74) Attorney, Agent, or Firm—Oblon, Spivak, McClelland, Maier & Neustadt, P.C.

(57) ABSTRACT

This invention is to provide a photoprotein which binds with a ligand specific for a substance to be detected at a binding ratio of 1:1 such that the luminescence activity is not reduced by binding with the ligand, a conjugate comprising the luminescent photoprotein and ligand, and a substance detection method which employs the conjugate as a marker. A calcium-binding photoprotein is produced having cysteine residue introduced within the 4th amino acid residue from the amino-terminus. A conjugate is formed by binding a ligand specific for a substance to be detected to the calcium-binding photoprotein, in a binding ratio of 1:1, via the introduced cysteine residue. The conjugate may be utilized as a marker for a substance to be detected.

14 Claims, 4 Drawing Sheets

Fig. 2

(kDa)
97.4-
69.0-
55.0-

36.5-

29.0-

20.1-

14.3-

RECOMBINANT PHOTOPROTEINS AND THEIR CONJUGATES

BACKGROUND OF THE INVENTION

1. Field of the Invention

The present invention relates to a recombinant calcium-binding photoprotein having a cysteine residue introduced in the amino-terminal region. It also relates to a conjugate wherein a ligand which binds specifically to a substance to be detected is bound via the cysteine residue, and to a method of detecting substances using the conjugate as a luminescence marker.

2. Related Background Art

The calcium-binding photoproteins emit a flash of light upon specific interaction with calcium, and the known calcium-binding photoproteins currently include aequorin, clytin, obelin, mitrocomin, mnemiopsin and berovin. These photoproteins are highly sensitive to calcium ion, while their luminescences are very high and detected extremely sensitively by commercial detection devices at very low detection limit, at less than 1 picogram. These photoproteins are therefore used for detection and quantification of trace calcium ion and as imaging probes for visualization of dynamic changes in intracellular calcium ion. Because the photoproteins exhibit their luminescence by specifically binding with calcium ion, the background signal which poses a problem for ordinary chemilumine scence is virtually absent and the luminescent reaction itself is instantaneous, going to completion within a few seconds, such that a rapid signal with a favorable S/N ratio is obtained.

Since luminescent reaction systems involve enzyme-mediated luminescent reactions, known as bioluminescence, and consist entirely of biological components, they contain no harmful chemical substances (such as radio isotopes or carcinogenic compounds) and are highly safe. Such photoproteins therefore hold much promise as markers for diagnostic agents and the like.

When using a calcium-binding photoprotein such as aequorin as a marker for immunoassay, for example, the marker must be linked with the substance to be detected. Specifically, the marker photoprotein must be either bound directly to the substance, or it must be indirectly bound thereto through some other substance. Throughout the present specification, a substance used to link a substance to be detected with a photoprotein (marker), either by direct or indirect binding with the substance to be detected, will be referred to as a "ligand". Such ligands include, for example, biotin, avidin, streptavidin, antigens, antibodies and the like, and will be explained in detail hereunder.

Because of the relatively unstable nature of calcium-binding photoproteins, they are prone to loss of luminescence activity when bound to their ligands. For more precise analytical and diagnostic results, the binding ratio of the photoprotein and its ligand is preferably exactly or nearly 1:1. A rapid and precise diagnosis/detection system may be established by using a ligand-photoprotein conjugate with the ligand and photoprotein bound at a ratio of 1:1.

A representative calcium-binding photoprotein is aequorin, obtained from *Aequorea aequorea*. Aequorin exists as a complex of the apoprotein portion, apoaequorin, the luminescent substrate, coelenterazine, and molecular oxygen. On binding of calcium to the aequorin molecule, a blue flash of light (maximum wavelength: 465 nm) is produced, and coelenteramide (the oxidized form of coelenterazine) and carbon dioxide are also produced. After the luminescent reaction, the calcium ion may be removed from apoaequorin by a chelating agent such as EDTA, and aequorin may be regenerated by incubation at low temperature in the presence a reducing agent, coelenterazine and molecular oxygen. Analysis of the gene coding for apoaequorin has identified that apoaequorin is composed of 189 amino acids. Its amino acid sequence is listed as SEQ. ID. No.1 of the Sequence Listing. Aequorin has a homologous sequence with the calcium-binding protein calmodulin, and has been reported to comprise three "EF hand motif" domains each comprising a helix-loop-helix structure, for calcium binding (Inouye et al., Proc. Natl. Acad. Sci. USA 82(1985): 3154–3158). Also, the results of X-ray crystallography suggest that the 184th tyrosine residue near the C-terminus is involved in stabilization of the peroxide portion of the luminescent substrate coelenterazine (Head et al., Nature 405(2000):372–376).

Biotin-avidin (or streptavidin) binding is the basis of one of the most commonly used diagnosis/detection systems for immunoassay, and successful biotinylation of aequorin has been reported (Zatta et al., Anal. Biochem. Vol. 194, pp. 185–191, 1991). The biotinylated aequorin produced by Zatta et al. was obtained by biotinylating a free amino group ($-NH_2$) in aequorin. The amino groups suspected of being modified by the method of Zatta et al. are one terminal amino group and amino groups of 15 lysines, but it has not been determined which of the amino groups are biotinylated in what proportion. Also, no method has been established for specifically modifying only one specific amino group. That is to say, high-quality biotinylated aequorin obtained by bonding biotin to aequorin via a free amino group, has not yet been provided.

Genetic analysis of calcium-binding photoproteins has revealed the presence of 3–6 cysteine residues in such molecules. Also X-ray structural analysis of aequorin and obelin has shown that none of the cysteine residues form disulfide bonds, but that all are present in a free state. It is further known that the luminescence activity of aequorin can be easily eliminated by modification with a low molecular chemical modifier, such as N-ethylmaleimide or iodoacetic acid, at the cysteine —SH group. (Shimomura et al., Biochemistry 13(1974):3278–3286).

The present inventors have previously reported luminescence activity by a cysteine-free mutant aequorin having the three cysteine residues in the molecule replaced with serine residues (K. Kurose et al., Proc. Natl. Acad. Sci. USA 86(1989):80–84). In another experiment, cysteine was substituted for the 5th serine, 53rd glutamic acid, 71st methionine and 84th glutamic acid in the apoaequorin of the cysteine-free mutant aequorin, and those new apoaequorins were used to form thyroxine-apoaequorin conjugates by binding thyroxine through cysteine and reconstituted to thyroxine-aequorin conjugates (Lewis et al., Bioconjugate Chem. 11:65–70 & 140–145(2000)). However, this involves substitution of serine for all of the three cysteine residues of wild-type aequorin and modification by introduction of new unique cysteine residue. As yet, no aequorin has been obtained which still exhibits luminescence activity with binding of the ligand to the —SH group of a newly introduced cysteine residue, while keeping the three original cysteine residues of wild-type aequorin.

The method of Lewis, et al., whereby aequorin is regenerated from modified (biotinilated) apoaequorin, produces a relatively low yield compared with the modification (biotinilation) of regenerated aequorin. Due to the nature of the mechanism by which the aequorin is regenerated, regeneration of modified aequorine cannot be applied to wide variety of modified apoaequorins but can be applied to apoaequorins modifed with specific modifying compounds with minimal influence on the regeneration process. Modification of regenerated aequorin, on the other hand, can be applied to any type of ligand molecules and thus the ligand molecules are not limited to a specific one. Another disadvantage of the method of Lewis et al. is that the ligand-aequorin conjugate, ligand-apoaequorin conjugate, unmodified aequorin and unmodified apoaequorin are not separated. Thus, a homogeneous ligand-aequorin conjugate wherein the ligand is bound to aequorin via the —SH group of the introduced cysteine residue, which is suitable for actual analysis, is yet to be produced.

SUMMARY OF THE INVENTION

It is an object of the present invention to provide a luminescent ligand-photoprotein conjugate by introducing cysteine residue into a calcium-binding photoprotein and binding it with its ligand via the cysteine —SH group in a binding ratio of exactly or nearly 1:1. It is another object of the invention to use the conjugate as a marker for immunoassay and the like.

The present inventors investigated photoprotein-ligand conjugates using aequorin as the calcium-binding photoprotein and biotin as the ligand. It was discovered, as a result, that by introducing one cysteine residue into the N-terminal region of the apoprotein of the calcium-binding photoprotein, and especially into the region from the N-terminus to the 4th amino acid residue of the wild-type photoprotein, it is possible to produce a photoprotein with luminescence activity equal to the original photoprotein, that binding the photoprotein with a ligand via —SH group of the introduced cysteine residue can produce a conjugate with a binding ratio of exactly or nearly 1:1, and that the conjugate can be used as a marker.

Since modification of any one of the three cysteines in the wild-type aequorin lowers the luminescence activity as explained above, a new cysteine residue must be introduced for binding of the ligand. Luminescence activity is also known to be lowered if the C-terminal region or C-terminal amino acids are altered (Nomura et al., FEBS Lett. 295 (1991):63–6%), and therefore introduction of a cysteine residue in the C-terminal region is not feasible. After considering the stability of aequorin itself, the regeneration efficiency from apoaequorin to aequorin, and the effect of cysteine residue introduction on the secondary structure of aequorin, it was attempted to introduce a cysteine residue within the 4th amino acid residue from the N-terminus of the wild-type apoaequorin. As a result it was found, surprisingly, that the obtained aequorin exhibited no reduced luminescence activity, that the ligand was bound only to the introduced cysteine residue with no effect whatsoever on the original three cysteines, and that the resulting ligand-aequorin conjugate maintains the original luminescence activity. The reasons for binding of the ligand only to the introduced cysteine residue and not to the original three cysteines are believed to be that (1) the introduced cysteine residue is near the N-terminus and therefore exposed on the surface of the protein molecule, (2) the three original cysteines are in the interior of the protein molecule, and (3) —SH group-modifying reagents for ligand binding are of a size which cannot easily reach the interior of the protein molecule.

All calcium-binding photoproteins share similar characteristics in that (1) coelenterazine is the substrate, (2) the apoprotein, coelenterazine and oxygen bind to form the photoprotein and (3) the photoprotein emits light by the action of calcium ion, generating the apoprotein with coelenteramide (oxidized coelenterazine) and carbon dioxide. Their amino acid sequences also have high homology. The results obtained for this aequorin, therefore, can be applied to all other calcium-binding photoproteins as well.

The present invention relates to a recombinant calcium-binding photoprotein comprising a wild-type or mutant apoprotein having one cysteine residue introduced within the 4th amino acid residue from the amino terminus of the wild-type apoprotein. A mutant protein, for the purposes of the present specification, is a protein modified by a deletion, substitution or addition of 1–5 amino acids in a range which conserves the introduced cysteine residue and does not impair the luminescence activity. The protein modification preferably conserves not only the introduced cysteine residue but also all of the cysteines of the wild-type photoprotein. This is because substitution of serine for the three cysteines of wild-type aequorin increases the time for regenerating aequorin from apoaequorin from 3 hours to 24 hours (K. Kurose et al., Proc. Natl. Acad. Sci. USA 86(1989) 80–84). It is also necessary to avoid alteration of sites essential for the calcium-binding structure and stabilization of the luminescent substrate. Known calcium-binding photoproteins include aequorin, obelin, clytin, mitrocomin, mnemiopsin and berovin. The cysteine-introduced calcium-binding photoprotein is produced by treating the cysteine-introduced apoprotein in the presence of the luminescent substrate coelenterazine and molecular oxygen. The luminescent substrate used may be either coelenterazine or a coelenterazine analog with luminescence activity.

The amino acid sequence of wild-type apoaequorin is listed as SEQ. ID. No.1 of the Sequence Listing. Cysteine residue is introduced in the region from the amino-terminal Val to the 4th Thr. Thus, one mode of the calcium-binding photoprotein of the invention is a recombinant calcium-binding photoprotein comprising an apoprotein having one cysteine residue introduced within the 4th amino acid residue from the amino terminus of the amino acid sequence of wild-type apoprotein listed as SEQ. ID. No.1 or its mutant apoprotein. Thus, cysteine residue may be inserted between the N-terminal Val and the 2nd Lys from the N-terminus, between the 2nd Lys and the 3rd Leu or between the 3rd Leu and the 4th Thr of the amino acid sequence listed as SEQ. ID. No.1. Alternatively, cysteine residue maybe substituted for the N-terminal Val, or the 2nd Lys, the 3rd Leu or the 4th Thr from the N-terminus. The cysteine is most preferably inserted between the 3rd Leu and 4th Thr.

The apoaequorin is produced by genetic engineering technique. For production of apoaequorin by a genetic engineering method, the outer membrane protein A (ompA) of *E. coli* maybe fused to the apoaequorin gene and expressed in *E. coli* cells for high-efficiency expression of apoaequorin. The product has an Ala-Asn-Ser- sequence instead of valine at the N-terminus of the wild-type apoaequorin but is equivalent to the wild-type apoaequorin in terms of calcium-binding ability and luminescence activity (Inouye et al., J. Biochem., 105,473–477(1989) and Inouye et al., Protein Expression and Purification 2, 122–126(1991)). Aequorin comprising mutant apoaequorin with Ala-Asn-Ser- at the N-terminus bound with coelenterazine and molecular oxygen is commercially available. In the mutant aequorin, cysteine may be introduced at any position in the region up to Thr at the 6th position from the N-terminus (4th from the wild-type N-terminus). That is, cysteine may be introduced at any position in the region from the N-terminal Ala to the 6th Thr in the mutant aequorin. A preferred example is mutant aequorin having cysteine residue introduced between the 5th Leu and 6th Thr, and this amino acid sequence is listed as SEQ. ID. No.2. This cysteine-introduced mutant aequorin may be modified by a deletion, substitution or addition of 1–5 amino acids in a range which conserves the 6th cysteine residue and maintains luminescence activity. Another preferred mode of the invention, therefore, is a recombinant calcium-binding photoprotein comprising an apoprotein having the amino acid sequence listed as SEQ. ID. No.2, or an apoprotein having the amino acid sequence listed as SEQ. ID. No. 2 modified by a deletion, substitution or addition of 1 to 5 amino acids such that the 6th cysteine residue is conserved and luminescence activity is maintained.

The calcium-binding photoprotein of the invention forms a conjugate by binding with a ligand specific for a substance to be detected. The invention relates to a conjugate where in a ligand specific for a substance to be detected binds to the aforementioned recombinant calcium-binding photoprotein via the aforementioned cysteine residue, in a ratio of 1:1. "Conjugation ratio of 1:1" between the photoprotein and ligand is not used in a strict sense, and means a ratio of either exactly or nearly 1:1.

A "ligand" as used according to the invention is a substance which binds either directly or indirectly to a substance to be detected. For example, it is a primary antibody where the detection involves an antigen site or antigen titer in an immunoassay. The primary antibody to which aequorin binds in turn binds to the antigen to be detected, such that measurement of aequorin luminescence allows detection of the antigen site or titer. In this case, the primary antibody acts as the ligand.

The use of secondary antibodies is also known for achieving increased sensitivity. A secondary antibody-bound biotin may be used for reaction with avidin or streptavidin-bound aequorin. In this case, avidin or streptavidin acts as the ligand. In order to take advantage of the fact that one molecule of avidin or streptavidin can bind four molecules of biotin, aequorin is bound with biotin. Four molecules of aequorin bind to one molecule of secondary antibody-bound avidinor streptavidine via the biotin, and therefore biotin is the ligand in this case.

For detection of a receptor, the signal peptide which binds to the receptor (a hormone such as insulin, or a cytokine, TNF, Fas ligand, etc.) will serve as the ligand. For detection of a signal peptide, a peptide of the receptor will serve as the ligand. For detection of a drug receptor, the drug will be the ligand, and for detection of a drug, the drug receptor will be the ligand.

For detection of an enzyme, its substrate serves as the ligand, and for detection of an enzyme substrate, the enzyme serves as the ligand. For detection of a nucleic acid which binds specifically to another nucleic acid, the complementary nucleic acid is the ligand. For detection of a substance which binds specifically to a polysaccharide, the polysaccharide is the ligand. Lectins capable of binding specifically to blood clotting factors or DNA-binding proteins such as transcription factors may also serve as ligands.

The conjugate may be produced by genetically producing a cysteine-introduced apoprotein, treating the apoprotein with coelenterazine in the presence of molecular oxygen to regenerate the recombinant calcium-binding photoprotein, and then binding the photoprotein via the introduced cysteine residue to a ligand specific for a substance to be detected, in a ratio of exactly or nearly 1:1. Any type of ligand may be bound to the calcium-binding photoprotein by the reaction of regenerated calcium-binding photoprotein with a lignad.

Because the conjugate binds specifically to a substance to be detected and emits light with calcium ion, it may be used as a marker for immunoassay and the like. The invention therefore also relates to a measuring method for substances specific for ligands and to kits for such measurement, which employ the aforementioned conjugate.

According to another mode, the invention relates to DNA coding for an apoprotein having cysteine residue introduced within the 4th amino acid residue from the amino terminus, to a recombinant expression vector comprising the DNA and to host cells transformed with the recombinant expression vector.

According to yet another mode, the invention relates to a method for producing the apoprotein of the invention using the aforementioned recombinant expression vector or recombinant host cells. Specifically, such a method comprises using the recombinant expression vector for in vitro expression or culturing the host cells, as well as isolation and purification of the apoprotein produced thereby. The invention still further relates to a method of producing the conjugate by treating the apoprotein with coelenterazine in the presence of molecular oxygen to regenerate the photoprotein, and binding the photoprotein with a ligand.

BRIEF DESCRIPTION OF THE DRAWINGS

FIG. 2 is a drawing showing the results of confirming cysteine-inserted aequorin purity by SDS-PAGE.

DETAILED DESCRIPTION OF THE PREFERRED EMBODIMENTS

Figure 1:
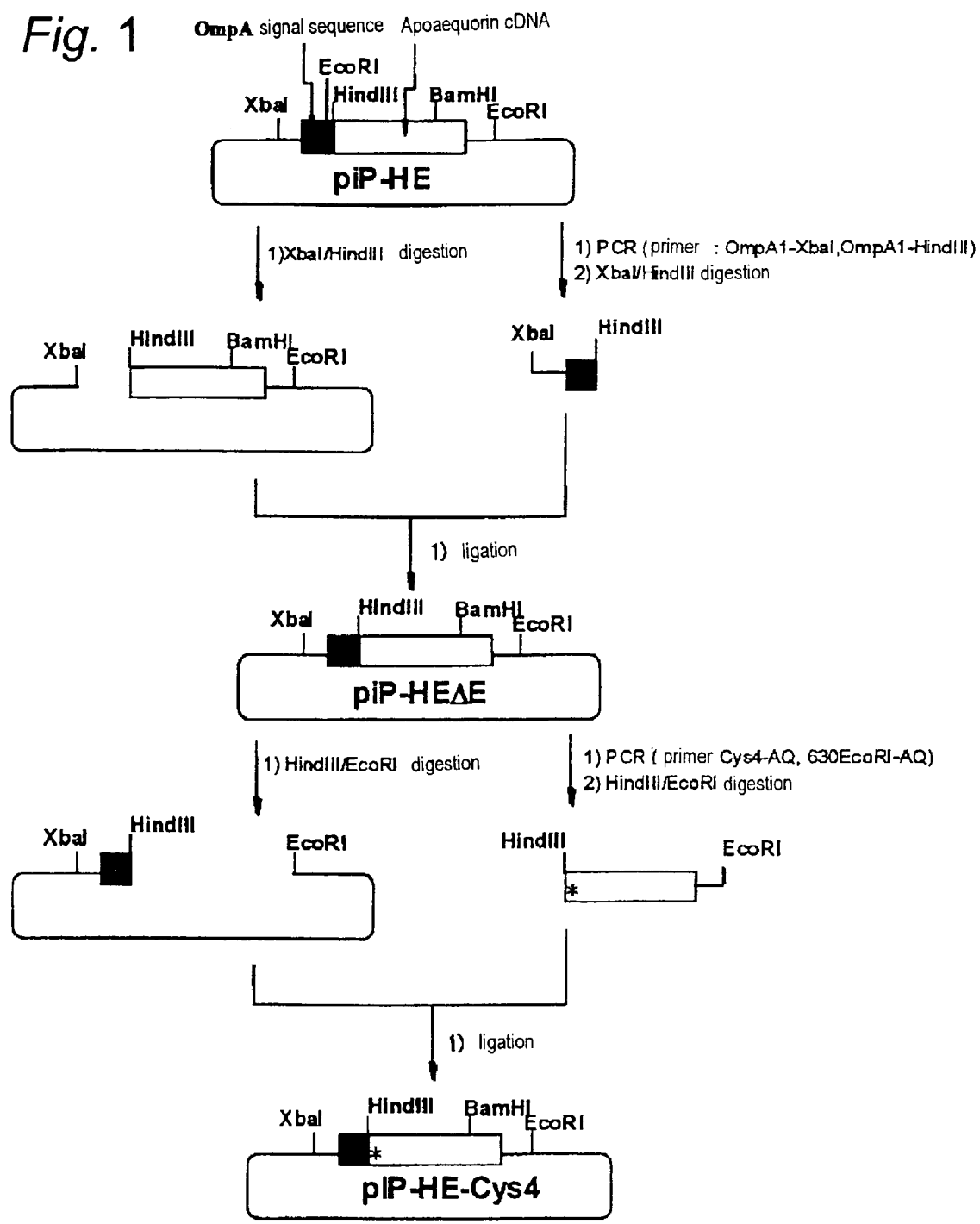
FIG. 1 is a schematic drawing illustrating construction of a cysteine-inserted aequorin expression vector.

Cysteine residue may be introduced at the N-terminus of a photoprotein either by a method of substituting cysteine for any of the 1–4 amino acids from the wild-type N-terminus or a method of inserting cysteine between any of the 1–4 amino acids, but cysteine insertion is preferred. Specifically, the cysteine residue may be introduced by a well-known technique in the field, such as PCR for introduction of a cysteine codon into the gene coding for the photoprotein. A recombinant expression vector is then prepared containing the resulting cysteine-introduced apoprotein gene, and the cysteine-introduced apoprotein is expressed in appropriate host cells.

The preferred apoprotein is apoaequorin. The apoaequorin used may be wild-type apoaequorin having the amino acid sequence listed as SEQ. ID. No.1, or a mutant thereof. A preferred mutant is one having an Ala-Asn-Ser- sequence instead of valine at the N-terminus of the wild-type apoaequorin. The cysteine residue may be introduced in the region up to the 4th amino acid Thr of the wild-type apoaequorin. When the mutant has an Ala-Asn-Ser- sequence instead of valine at the N-terminus, the cysteine residue may be introduced at any position from the N-terminal Ala up to the 6th amino acid Thr. The most preferred cysteine-introduced apoaequorin of the invention has cysteine residue introduced between the 5th Leu and the 6th Thr of the aforementioned mutant, which has the amino acid sequence listed as SEQ. ID. No.2.

According to the invention, the vector used for expression of the photoprotein may be a vector suitable for a cell-free expression system (in vitro transcription-translation) or a protein expression system using host cells such as *E. coli*, yeast or cultured animal cells. Such a vector may be purchased or easily created from a publicly known vector. For example, a vector for expression by in vitro translation or in cultured animal cells may be pTargetT vector incorporating the immediate-early enhancer/promoter region of human cytomegalovirus with the T7 promoter sequence/multicloning site downstream therefrom or pSI vector comprising the SV40 enhancer and SV40 early promoter (Promega), or pBK-CMV, CMV-Script, pCMV-Tag or pBK-RSV (Stratagene). A vector for expression in microbial cells such as *E. coli* or yeast may be, for example, a pET series vector expression system comprising T7 promoter for an *E. coli* system (for example, pET3a, pET27b(+) or pET28a(+); Novogene), or a *Pichia* system pIC series expression vector comprising alcohol oxidase promoter for a yeast system (for example, pPIC9K or PIC3.5K; Invitrogen).

The recombinant expression vector containing the cysteine-introduced apoaequorin gene is used to transform appropriate host cells, and the host cells are cultured and the expressed apoaequorin isolated. The cysteine-introduced apoaequorin is treated with coelenterazine in the presence of molecular oxygen to regenerate cysteine-introduced aequorin. By using a coelenterazine derivative (analog compound) instead of coelenterazine as the luminescent substrate, it is possible to produce semi-synthetic aequorin with luminescence activity. Semi-synthetic aequorins have been reported which differ in calcium response or give an improved S/N ratio, with respect to wild-type aequorin (Shimomura et al., Biochem. J. Vol. 296, pp.549–551, 1993). The regenerated aequorin may be purified by hydrophobic chromatography, for example, to obtain high-purity cysteine-introduced aequorin containing no unpurified apoaequorin.

The cysteine-introduced aequorin may be bound to its specific ligand via the —SH group of the introduced cysteine residue. The means of binding with the specific ligand will differ depending on the physical and chemical properties of the ligand. Depending on the size of the aequorin molecule and steric hindrance with the ligand, the cysteine-intriduced aequorin may be bound to the ligand either directly or via a linker or spacer.

There are no particular restrictions on a linker or spacer to be used according to the invention so long as it can react specifically with the —SH group, but it is preferably one with a length of 20 angstroms or greater. A variety of —SH group-modifying reagents are commercially available for use as linkers or spacers, and may be selected as appropriate. The reaction of binding the ligand to the cysteine-introduced aequorin is preferably carried out at no higher than 30° C. and preferably no higher than 25° C., and at a pH of 6–8 and preferably a pH of 6–7.5.

The present invention will now be explained in greater detail by examples using aequorin as the photoprotein, with the understanding that the examples are not intended to be limitative on the invention.

EXAMPLES

Example 1

Construction of Cysteine-Inserted Apoaequorin Expression Vector

From expression vector piP-HE for mutant apoaequorin having an Ala-Asn-Ser sequence instead of valine at the N-terminus of the wild-type apoaequorin (J. Biochem. 105, 473–477(1989)), the EcoRI restriction enzyme site near the N-terminus of the apoaequorin gene was deleted by PCR to construct piP-HEΔE. A cysteine residue was introduced at the 6th position from the N-terminus of the mutant apoaequorin (the 4th position from the N-terminus of the wild-type apoaequorin) by PCR to construct the cysteine-inserted aequorin gene expression vector piP-HE-Cys4. FIG. 1 shows the specific construction scheme.

There were used 0.1 μg of piP-HE plasmid as the template and 1 μg each of the PCR primers OmpA1-XbaI (5'TGG-AAC-TCT-AGA-TAA-CGA-GGG-CAA-AAA3', SEQ. ID. No.3) and OmpA1-HindIII (5'TCC-AAG-CTT-GGA-GTT-CGC-GGC-CTG3', SEQ. ID. No.4). A DNA Thermal Cycler (Perkin Elmer) and a GeneAmp PCR reagent kit containing AmpliTaq DNA polymerase (Takara Shuzo) were used for PCR amplification of the target fragment, and then the fragment was separated with a PCR purification kit (Qiagen) and digested with restriction enzymes XbaI and HindIII, upon which an XbaI-HindIII fragment lacking the EcoRI restriction enzyme site was obtained. Separately, plasmid piP-HE was digested with restriction enzymes XbaI and HindIII, and the apoaequorin gene-containing vector portion was isolated with a DNA purification kit (Qiagen). This was linked with the amplified XbaI-HindIII fragment and the obtained plasmid was used to transform *E. coli* JM83. The EcoRI site-deficient plasmid piP-HEΔE was isolated from the transformants. The gene sequence was confirmed with a Taq DyeDeoxy Terminator Cycle Sequencing Kit (Applied Biosystems) and a DNA 377 Sequencer (Applied Biosystems). The amino acid sequence was identical to the original mutant except for the lack of the EcoRI site.

Next, there were used 0.1 μg of piP-HELE plasmid as the template and 1 μg each of the PCR primers Cys4-AQ (5'GGC-AAG-CTT-TGT-ACT-AGT-GAC-TTC-GAC-AAC-CCA-AGA-TGG3', SEQ. ID. No.5) and 630EcoRI-AQ (5'GCC-GAA-TTC-ATC-AGT-GTT-TTA-TTC-AAA3', SEQ. ID. No.6) for PCR amplification of the target fragment with a GeneAmp PCR reagent kit (Takara Shuzo), followed by isolation of the fragment with a purification kit (Qiagen) and digestion with restriction enzymes HindIII and EcoRI to obtain a HindIII-EcoRI fragment with cysteine at the 6th position from the N-terminus of the mutant apoaequorin gene (4th position from the N-terminus of the wild-type apoaequorin gene). Separately, plasmid piP-HEΔE was digested with restriction enzymes HindIII and EcoRI, and the vector end containing the promoter and OmpA signal peptide was isolated. This was linked with the HindIII-EcoRI fragment and the obtained plasmid was used to transform *E. coli* JM83. Plasmid piP-HE-Cys4 expressing the mutant apoaequorin with cysteine inserted at the 6th position from the N-terminus was isolated from the transformants. The base sequence was determined with a Taq DyeDeoxy Terminator Cycle Sequencing Kit (Applied Biosystems) and a DNA 377 Sequencer (Applied Biosystems), and confirmed to be the cysteine-inserted apoaequorin (Cys4-apoaequorin). The amino acid sequence of Cys4-apoaequorin is listed as SEQ. ID. No.2.

Example 2

Separation of Cysteine-Inserted Apoaequorin-Producing Strain

The recombinant plasmid piP-HE-Cys4 produced in Example 1 was used as the expression vector for transformation of E. coli WA802 as the host according to an ordinary procedure. After culturing 20 transformants overnight at 30° C. in LB agar medium (10 g bactotryptone, 5 g yeast extract, 5 g sodium chloride in 1 L water, pH 7.2), they were transferred to LB liquid medium containing 5 mL of ampicillin (50 µg/mL) and further cultured at 37° C. for 16 hours. The strain with the highest luminescence activity, i.e. the highest Cys4-apoaequorin-producing strain, was selected and used for larger-scale culturing of a high luminescence activity strain.

Example 3

Culturing of Cysteine-Inserted Apoaequorin-Producing Strain

The Cys4-apoaequorin-producing strain was cultured overnight at 30° C. and then transferred to LB liquid medium containing 50 mL of ampicillin (50 µg/mL). After further culturing at 30° C. for 8 hours, it was transferred into 2 L of fresh LB liquid medium and cultured overnight (18 hours) at 37° C. The cells and culturing solution were separated by low-speed centrifugation (5000×g). The cells and culturing solution both contained the expressed apoaequorin and therefore both were stored as the starting materials for Cys4-apoaequorin purification.

Example 4

Regeneration and Purification of Cysteine-Inserted Aequorin From Cells

The collected cells were suspended in 400 mL of buffer solution (50 mM Tris-HCl, 10 mM EDTA, pH 7.6) containing 200 mg of dithiothreitol, a reducing agent (Wako Pure Chemical Industries) After disrupting the cells by ultrasonic treatment for 2 minutes while cooling on ice, they were centrifuged for 20 minutes (12,000×g) and the supernatant was collected. Chemically synthesized coelenterazine dissolved in a small amount of methanol was added to the supernatant to a 1.2-fold molar concentration with respect to the Cys4-apoaequorin, and the mixture was allowed to stand at 4° C. for more than 5 hours. The obtained supernatant liquid was immediately adsorbed onto a Q-Sepharose column (2 cm diameter×10 cm, Pharmacia) equilibrated with a column buffer solution (20 mM Tris-HCl, 10 mM EDTA, pH 7.6) and the column was washed with a buffer solution containing 0.1 M NaCl until the absorbance of the eluate at 280 nm fell below 0.05. The column-adsorbed fraction containing both the unregenerated Cys4-apoaequorin and the regenerated Cys4-aequorin was eluted by a 0.1–0.4 M NaCl linear concentration gradient.

The regenerated Cys4-aequorin and unregenerated Cys4-apoaequorin were separated in the following manner using Butyl Sepharose 4 Fast Flow Gel chromatography.

Ammonium sulfate was added to the orange eluate from the Q-Sepharose column to a final concentration of 2 M. After this addition the insoluble fraction was removed by centrifugation. The supernatant was then added to Butyl Sepharose 4 Fast Flow (column size: 2 cm diameter×8 cm, Pharmacia) equilibrated with the aforementioned column buffer solution containing 2 M ammonium sulfate and eluted with a 2-1 M ammonium sulfate linear concentration gradient, upon which an orange fraction containing the luminescence active, or regenerated, Cys4-aequorin was collected. The unregenerated Cys4-apoaequorin was separately eluted with the column buffer alone.

Figure 2:
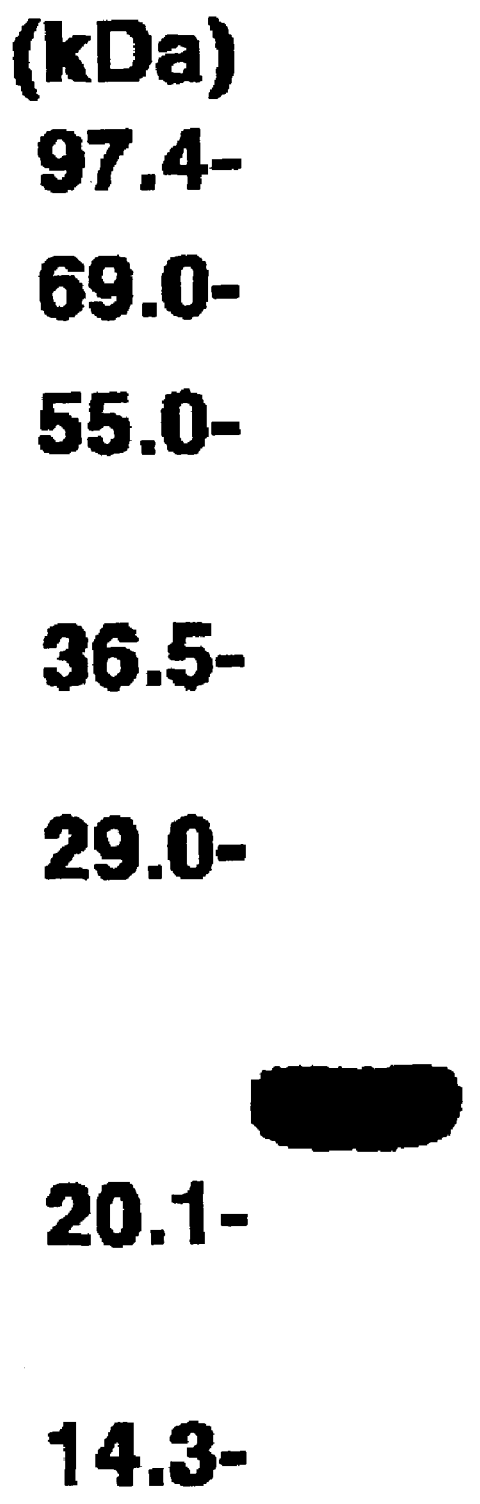

The purity of the purified fraction was examined by 12% SDS-PAGE. This revealed a single band of the purified fraction corresponding to a 25 kDa protein, the purity of which was measured with a densitometer to be ≧98% (FIG. 2). Upon determining the purified protein concentration by the Bradford method (Biorad) using bovine serum albumin as a standard sample, the yield was 44.6 mg of high-purity Cys4-aequorin from 2L of the cultur solution.

Example 5

Regeneration and Purification of Cysteine-Inserted Aequorin From Culture Solution The ≧98% purity apoaequorin was obtained from the culture solution and used to regenerate and purify aequorin in the same manner as Example 4. The purified aequorin was analyzed by 12% SDS-PAGE, giving the same results as in Example 4. The yield was 10.4 mg of high-purity Cys4-aequorin from 2 L of the culture solution.

Example 6

Preparation of Biotinylated Cys4-Aequorin by Maleimide-Activated Biotin

The purified Cys4-aequorin and 1.2–3 molar equivalents of maleimide-activated biotin were incubated for 2 hours in PBS solution (10 mM phosphate buffer, 2.7 mM KCl, 137 mM NaCl, pH 7.4) at a reaction temperature of 0-20° C. for specific biotinylation of the cysteine residue inserted at the N-terminus. The procedure was conducted as follows.

After adding 4 µl (30 nmol) of maleimide-activated biotin (EZ-Link PEO-Maleimide-activated Biotin, Pierce: spacer length=29.1 angstroms) dissolved in PBS solution to 800 µl of PBS solution in a 1.5 ml polypropylene tube, 200 µl (100 nmol) of Cys4-aequorin was further added to initiate modification reaction, and reaction was conducted for 2 hours at 20° C. in the dark. Every 30 minutes during the modification reaction, 1 µl of reaction solution was taken and dot blotted on a nitrocellulose membrane (Biorad) for confirmation of biotinylation by the dot blot coloring method using anti-biotin rabbit antibody-alkali phosphatase (Sigma). Though biotinylation occurred rapidly from 0–1 hour, no notable increase in biotinylation was detected from 2 hours and onward. Aequorin without cysteine inserted was used as a control for biotinylation under the same conditions, but virtually no biotinylation was detected, thus demonstrating that biotinylation reaction had occurred only with the newly inserted cysteine residue.

It was shown that direct binding of ligands other than biotin, such as antibodies, antigens, low molecular organic compounds and the like, is possible by maleimide-type modification with a spacer of 20 angstroms or greater.

Also, when the luminescent activities of obtained biotinylated Cys4-aequorin and unreacted Cys4-aequorin were compared, virtually no reduction in luminescence activity was observed by the biotinylation, with the biotinylated Cys4-aequorin maintaining a luminescence activity of 96%. Moreover, when the reaction temperature was increased above 30° C. in the same reaction system, the luminescence activity fell to below 50% at 2 hours of reaction. Conducting the reaction at a pH of 8 or higher also lowered the luminescence activity to below 50% at 2 hours of reaction.

The cysteine-inserted aequorin biotinylation reaction is therefore preferably conducted at a temperature of no greater than 30° C. and more preferably no greater than 25° C., and at a pH of 6–8 and more preferably at a pH of 6–7.5.

The removal of the unreacted reagent, isolation of the biotinylated Cys4-aequorin and buffer solution exchange after the reaction were carried out in a single step of centrifugal filtration using Centricon 10 (Amicon) at 4° C. This step has the advantage of allowing replacement of the buffer solution according to the type of reaction system employed. In order to prevent reduction in luminescence activity, the protein concentration is kept/stored at 100 ng/mL or greater at a temperature of no higher than −80° C. This will prevent any notable reduction in activity for at least 6 months.

Example 7

Preparation of Biotinylated Cys4-Aequorin by Iodoacetyl-Activated Biotin

Biotinylation using iodoacetyl-activated biotin was conducted in the following manner as another representative specific modification method for cysteine (—SH) residue.

After adding 15 nmol of Cys4-aequorin to 800 µl of 50 mM Tris-HCl buffer (pH 8.0) containing 40 nmol of iodoacetyl-activated biotin (EZ-Link PEO-Iodoacetyl Biotin, Pierce: spacer length=24.8 angstroms), reaction was conducted for 2 hours at 20° C. in the dark. Every 30 minutes during the modification reaction, 1 µl of reaction solution was taken and dot blotted on a nitrocellulose membrane (Biorad) for confirmation of biotinylation by the dot blot coloring method using anti-biotin rabbit antibody-alkali phosphatase (Sigma). Though biotinylation occurred rapidly from 0–1 hour, no notable increase in biotinylation was detected from 2 hours and onward. Aequorin without cysteine inserted was used as a control for biotinylation under the same conditions, but virtually no biotinylation was detected, thus demonstrating that biotinylation reaction had occurred only with the newly inserted cysteine residue.

When the luminescent activities of obtained biotinylated Cys4-aequorin and unreacted Cys4-aequorin were compared, the biotinylated Cys4-aequorin was found to retain 88% luminescence activity. This indicates that specific biotinylation at a newly inserted cysteine residue is possible not only by addition reaction by the maleimide method but also by substitution reaction. It was shown that direct binding of ligands other than biotin, such as antibodies, antigens, low molecular organic compounds and the like, is possible by iodoacetyl-type modification with a spacer of 20 angstroms or greater.

Example 8

Determining Number of Bonds in Biotinylated Cys4-Aeguorin

The number of biotin bonds per protein molecule in the biotinylated Cys4-aequorin obtained in Example 4 was confirmed. For confirmation, the molecular weight was measured by matrix-assisted laser desorption ion time-of-flight mass spectrometry (MALDI-TOF-MS) using a Voyager DE Promass Spectrometer (PerSeptive Biosystem). This method allows separation of biotinylated and non-biotinylated cysteine-inserted aequorin, to determine the number of biotin bonds.

The calculated average molecular weight (m/z) for the Cys4-aequorin is 21,735.34, and the calculated average molecular weights for cysteine-inserted aequorin biotinylated at 1, 2 and 3 sites are 22,260.96, 22,786.58 and 23,312.20, respectively. Angiotensin I (m/z 1296.69), insulin (m/z 5734.59), apomyoglobin (m/z 16,952.60) and apoaequorin (m/z 2163.20) were used as molecular weight standards. The matrix used was prepared from α-cyano-4-hydroxycinnamic acid (Aldrich) and sinapic acid (Aldrich). A mixture of 1.5 µl of matrix solution and 0.5 µl of measuring sample was air-dried, and the mixture was supplied for molecular weight measurement. As a result, peaks were detected at 21,723.12, 22,252.23 and 22,474.56 corresponding to the molecular weights of unreacted Cys4-aequorin, Cys4-aequorin biotinylated at only one site, and a conjugate of Cys4-aequorin biotinylated at only one site with sinapic acid. The peak ratio was 4.9:69.6:25.5. Absolutely no Cys4-aequorin biotinylated at 2 sites was detected. These results demonstrated that, with less than 5% unreacted Cys4-aequorin, one biotin molecule reacts with one molecule of Cys4-aequorin at an efficiency of greater than 95%. This method therefore achieves stable and highly efficient production of biotinylated aequorin with a binding ratio of 1:1.

Example 9

Examination of Biotinylated Cys4-Aequorin

1) Comparison of Luminescence Patterns

Figure 3:
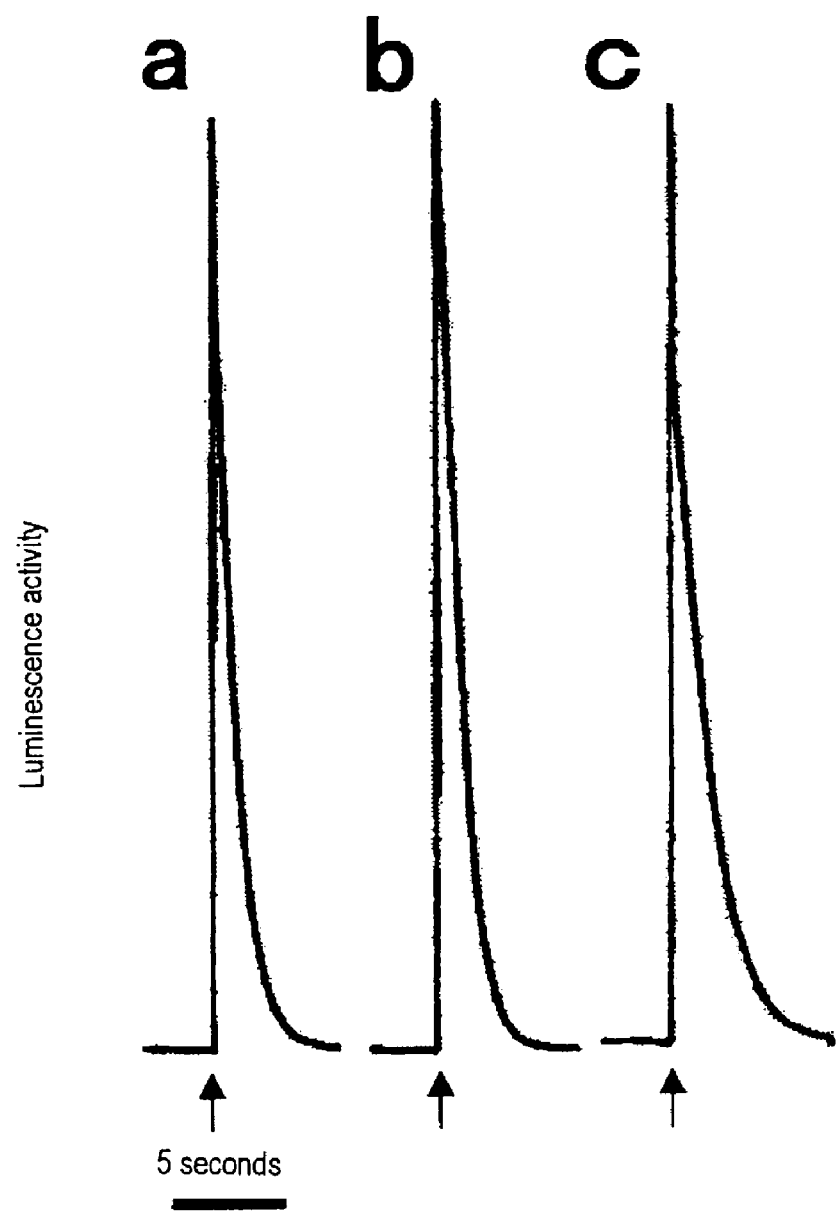
FIG. 3 shows luminescence and flash luminescence patterns for (a) non-cysteine-inserted aequorin, (b) Cys4-aequorin and (c) biotinylated Cys4-aequorin.

After adding 100 µl of a 50 mM calcium chloride solution to 1 ng of non-cysteine-inserted recombinant aequorin, Cys4-aequorin or biotinylated Cys4-aequorin, the luminescence and flash luminescence patterns were measured using a luminometer (TD-4000, Laboscience) (FIG. 3). In the drawing, a represents non-cysteine-inserted recombinant aequorin, b represents Cys4-aequorin and c represents biotinylated Cys4-aequorin. There was no change between the three luminescences and luminescence patterns, clearly demonstrating that no reduction in luminescence activity or difference in response to calcium occurs by biotinylating modification of the cysteine residue.

Figure 4:
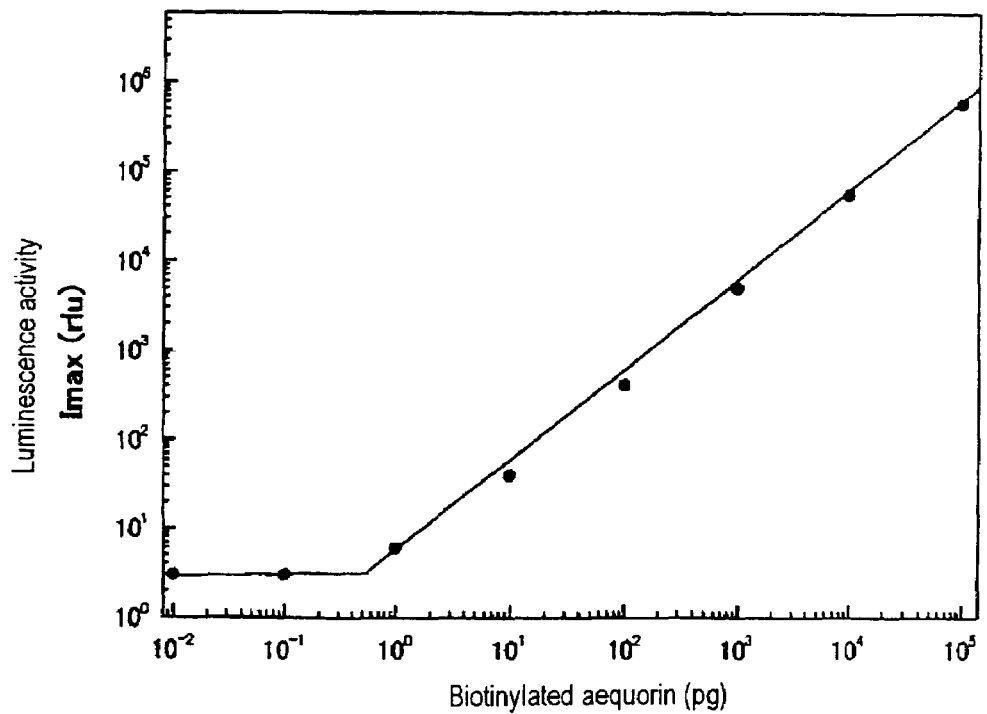
FIG. 4 is a graph showing the detection limit and luminescence activity with respect to protein concentration for biotinylated Cys4-aequorin.

2) Quantitation of biotinylated Cys4-aequorin The detection limit and linearity with respect to protein concentration for biotinylated Cys4-aequorin was examined. The biotinylated protein concentration was diluted in a range from 10 femtograms to 100 nanograms, a 50 mM calcium chloride solution (100 µl) was added, and the luminescence intensity (initial luminescence intensity maximum: Imax) was measured with a luminometer (Model AB2200, Atto). The linearity was confirmed by plotting the mean values for 3 measurements (FIG. 4). The detection limit for biotinylated Cys4-aequorin was under 1 picogram, and was therefore equivalent to recombinant aequorin having no introduced cysteine.

Example 10

Detection of Avidin Using Biotinylated Cys4-Aequorin

Figure 5:
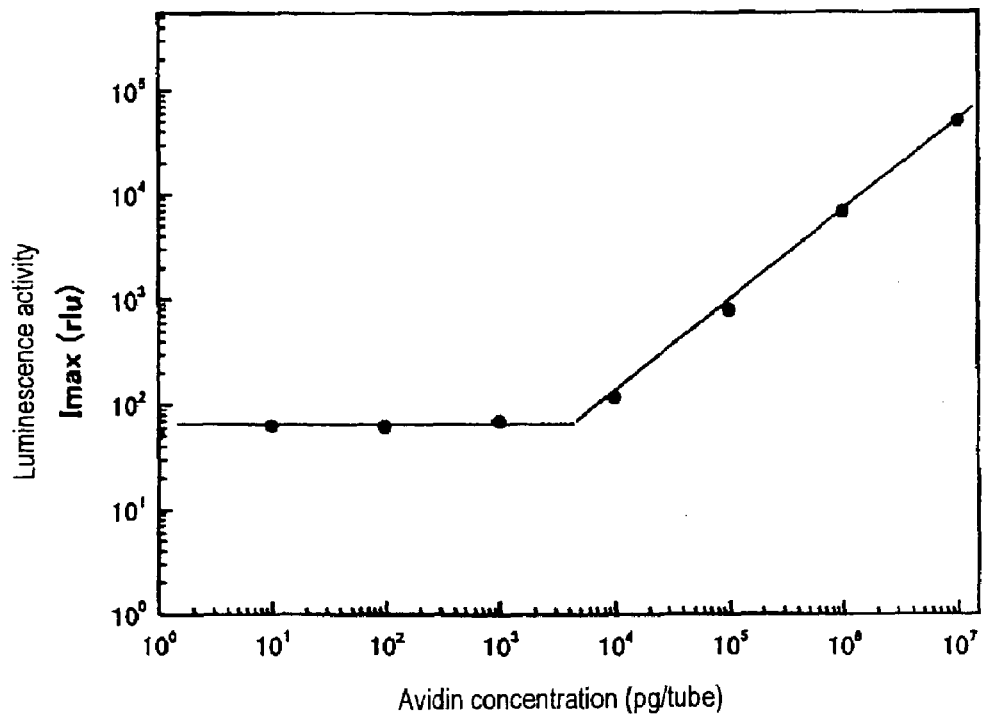
FIG. 5 is a graph showing the results of quantitating avidin using biotinylated Cys4-aequorin.

It was confirmed by direct binding whether the biotin portion of biotinylated Cys4-aequorin recognizes avidin and can be used for its detection in a quantitative manner. After diluting a stock solution (1 mg/ml) containing avidin (Wako Pure Chemical Industries) dissolved in TBST solution (20 mM Tris-HCl, pH 7.4, 150 mM NaCl, 0.05% Tween 20), it was dispensed into 5 ml immunoassay PolySorb tubes (Nunc) at concentrations from 1 picogram to 1 microgram, and the avidin was adsorbed onto the tubes. Separately, a 1% bovine serum albumin (Fraction V, Seikagaku Corp.) solution was prepared using TBST-EDTA solution (10 mM EDTA-containing TBST solution). The avidin-adsorbed tubes were then coated with 200 μl of the 1% bovine serum albumin solution to prevent non-specific adsorption. After adding 5 μl of biotinylated cysteine-inserted aequorin (100 μg/ml) and 100 μl of 1% bovine serum albumin-containing TBST-EDTA solution to each of the tubes, they were allowed to stand at room temperature for 20 minutes and then rinsed 3 times with 500 μl of TBST-EDTA solution. The rinsed tubes were each placed in a luminometer (Model AB2200, Atto), 100 μl of 50 mM calcium chloride solution was poured therein, and the initial luminescence intensity maximum (Imax) was measured. Each measurement was performed 3 times and the mean values were plotted (FIG. 5). Direct binding was exhibited with linearity at 10 nanograms or greater of the biotinylated Cys4-aequorin, thereby allowing quantitation of avidin. The biotinylated Cys4-aequorin of the invention was thus shown to be useful for immunoassay based on biotin-avidin binding.

What is claimed is:

1. A recombinant calcium-binding photoprotein aequorin, comprising a mutant apoaequorin having the amino acid sequence listed as SEQ. ID. No.2.

2. The recombinant calcium-binding photoprotein aequorin according to claim 1, comprising as luminescent substrate coelenterazine or its analog which exhibits the luminescence activity.

3. A conjugate, which comprises a recombinant calcium-binding photoprotein aequorin and a ligand specific for a substance to be detected, wherein said recombinant calcium-binding photoprotein aequorin comprises a mutant apoaequorin having the amino acid sequence listed as SEQ. ID. No. 2 and said ligand binds to said recombinant calcium-binding photoprotein aecluorin via the 6th cysteine, in a ratio of the ligand and the recombinant calcium-binding photoprotein aequorin being 1:1.

4. The conjugate according to claim 3, wherein the ligand specific for a substance to be detected is biotin, avidin, streptavidin, an enzyme, a substrate, an antibody, an antigen, nucleic acid, a polysaccharide, a receptor or a compound capable of binding to any of these.

5. A kit for measuring a substance specific for a ligand, comprising a conjugate according to claim 4.

6. The conjugate according to claim 3, comprising as luminescent substrate coelenterazine or its analog which exhibits the luminescence activity.

7. A kit for measuring a substance specific for a ligand, comprising a conjugate according to claim 6.

8. The conjugate according to claim 3, wherein the ligand specific for a substance to be detected is biotin.

9. A kit for measuring a substance specific for a ligand, comprising a conjugate according to claim 8.

10. A method for measuring a substance specific for a ligand, characterized by using a conjugate according to claim 3.

11. A kit for measuring a substance specific for a ligand, comprising a conjugate according to claim 3.

12. A kit for measuring a substance specific for a ligand, comprising a conjugate according to claim 3.

13. A method for producing a conjugate, which comprises producing by genetic engineering a mutant apoaequorin having the amino acid sequence listed as SEQ. ID. No.2, treating the apoaequorin with coelenterazine in the presence of oxygen to yield a recombinant calcium-binding photoprotein, and binding the photoprotein via the 6th cysteine to a ligand specific for a substance to be detected, in a ratio of the ligand and the recombinant calcium-binding photoprotein aequorin being 1:1.

14. The method for producing a conjugate according to claim 13, wherein the ligand specific for a substance to be detected is biotin.

* * * * *

SEQUENCE LISTING

```
<160> NUMBER OF SEQ ID NOS: 6

<210> SEQ ID NO 1
<211> LENGTH: 189
<212> TYPE: PRT
<213> ORGANISM: Aequorea aequorea

<400> SEQUENCE: 1

Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser
            20                  25                  30

Leu Asp Glu Met Val Tyr Lys Ala Ser Asp Ile Val Ile Asn Asn Leu
        35                  40                  45

Gly Ala Thr Pro Glu Gln Ala Lys Arg His Lys Asp Ala Val Glu Ala
    50                  55                  60

Phe Phe Gly Gly Ala Gly Met Lys Tyr Gly Val Glu Thr Asp Trp Pro
65                  70                  75                  80

Ala Tyr Ile Glu Gly Trp Lys Lys Leu Ala Thr Asp Glu Leu Glu Lys
                85                  90                  95

Tyr Ala Lys Asn Glu Pro Thr Leu Ile Arg Ile Trp Gly Asp Ala Leu
            100                 105                 110

Phe Asp Ile Val Asp Lys Asp Gln Asn Gly Ala Ile Thr Leu Asp Glu
        115                 120                 125

Trp Lys Ala Tyr Thr Lys Ala Ala Gly Ile Ile Gln Ser Ser Glu Asp
    130                 135                 140

Cys Glu Glu Thr Phe Arg Val Cys Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Cys Glu Lys Leu Tyr Gly Gly Ala Val Pro
            180                 185

<210> SEQ ID NO 2
<211> LENGTH: 192
<212> TYPE: PRT
<213> ORGANISM: Aequorea aequorea

<400> SEQUENCE: 2

Ala Asn Ser Lys Leu Cys Thr Ser Asp Phe Asp Asn Pro Arg Trp Ile
1               5                   10                  15

Gly Arg His Lys His Met Phe Asn Phe Leu Asp Val Asn His Asn Gly
            20                  25                  30
```

-continued

Lys Ile Ser Leu Asp Glu Met Val Tyr Lys Ala Ser Asp Ile Val Ile
            35                  40                  45

Asn Asn Leu Gly Ala Thr Pro Glu Gln Ala Lys Arg His Lys Asp Ala
        50                  55                  60

Val Glu Ala Phe Phe Gly Gly Ala Gly Met Lys Tyr Gly Val Glu Thr
65                  70                  75                  80

Asp Trp Pro Ala Tyr Ile Glu Gly Trp Lys Lys Leu Ala Thr Asp Glu
                85                  90                  95

Leu Glu Lys Tyr Ala Lys Asn Glu Pro Thr Leu Ile Arg Ile Trp Gly
            100                 105                 110

Asp Ala Leu Phe Asp Ile Val Asp Lys Asp Gln Asn Gly Ala Ile Thr
        115                 120                 125

Leu Asp Glu Trp Lys Ala Tyr Thr Lys Ala Ala Gly Ile Ile Gln Ser
130                 135                 140

Ser Glu Asp Cys Glu Glu Thr Phe Arg Val Cys Asp Ile Asp Glu Ser
145                 150                 155                 160

Gly Gln Leu Asp Val Asp Glu Met Thr Arg Gln His Leu Gly Phe Trp
                165                 170                 175

Tyr Thr Met Asp Pro Ala Cys Glu Lys Leu Tyr Gly Gly Ala Val Pro
            180                 185                 190

<210> SEQ ID NO 3
<211> LENGTH: 27
<212> TYPE: DNA
<213> ORGANISM: Artificial Sequence
<220> FEATURE:
<223> OTHER INFORMATION: PCR primer

<400> SEQUENCE: 3
tggaactcta gataacgagg gcaaaaa                                27

<210> SEQ ID NO 4
<211> LENGTH: 24
<212> TYPE: DNA
<213> ORGANISM: Artificial Sequence
<220> FEATURE:
<223> OTHER INFORMATION: PCR primer

<400> SEQUENCE: 4
tccaagcttg gagttcgcgg cctg                                  24

<210> SEQ ID NO 5
<211> LENGTH: 39
<212> TYPE: DNA
<213> ORGANISM: Artificial Sequence
<220> FEATURE:
<223> OTHER INFORMATION: PCR primer

<400> SEQUENCE: 5
ggcaagcttt gtactagtga cttcgacaac ccaagatgg                  39

<210> SEQ ID NO 6
<211> LENGTH: 27
<212> TYPE: DNA
<213> ORGANISM: Artificial Sequence
<220> FEATURE:
<223> OTHER INFORMATION: PCR primer

<400> SEQUENCE: 6
gccgaattca tcagtgtttt attcaaa                               27